US005743261A

United States Patent [19]
Mainiero et al.

[11] Patent Number: 5,743,261
[45] Date of Patent: *Apr. 28, 1998

[54] METHODS AND APPARATUS FOR THE INVASIVE USE OF OXIMETER PROBES

[75] Inventors: Louis M. Mainiero, Delafield; Stephen H. Gorski, Eage; Robert L. Young, Waukesha, all of Wis.

[73] Assignee: Sensor Devices, Inc., Waukesha, Wis.

[*] Notice: The term of this patent shall not extend beyond the expiration date of Pat. No. 5,417,207.

[21] Appl. No.: 412,287

[22] Filed: Mar. 28, 1995

Related U.S. Application Data

[63] Continuation-in-part of Ser. No. 163,052, Dec. 6, 1993, Pat. No. 5,417,207.

[51] Int. Cl.⁶ .................................................. A61B 5/00
[52] U.S. Cl. .................................................. 128/633
[58] Field of Search ........................... 128/632–634, 128/637, 664–667; 356/39–41

[56] References Cited

U.S. PATENT DOCUMENTS

| Re. 31,377 | 9/1983 | Mylrea et al. | 128/642 |
|---|---|---|---|
| 3,734,094 | 5/1973 | Calinog | 128/2.06 E |
| 3,951,136 | 4/1976 | Wall | 128/2.06 E |
| 4,176,660 | 12/1979 | Mylrea et al. | 128/671 |
| 4,301,809 | 11/1981 | Pinchak | 128/695 |
| 4,349,031 | 9/1982 | Perlin | 128/642 |
| 4,475,555 | 10/1984 | Linder | 128/670 |
| 4,476,872 | 10/1984 | Perlin | 128/642 |
| 4,484,583 | 11/1984 | Graham | 128/671 |
| 4,574,807 | 3/1986 | Hewson et al. | 128/419 |
| 4,830,014 | 5/1989 | Goodman et al. | 128/665 |
| 4,930,521 | 6/1990 | Metzger et al. | 128/786 |
| 4,960,133 | 10/1990 | Hewson | 128/784 |
| 4,981,470 | 1/1991 | Bombeck, IV | 128/635 |
| 5,052,390 | 10/1991 | Hewson | 128/419 D |
| 5,154,387 | 10/1992 | Trailer | 128/784 |
| 5,193,544 | 3/1993 | Jaffe | |
| 5,217,012 | 6/1993 | Young et al. | 128/633 |
| 5,247,932 | 9/1993 | Chung et al. | 128/633 |
| 5,282,464 | 2/1994 | Brain | 128/634 |
| 5,329,922 | 7/1994 | Atlee, III | 128/632 |
| 5,357,954 | 10/1994 | Shigezawa et al. | 128/634 |
| 5,411,024 | 5/1995 | Thomas et al. | |
| 5,417,207 | 5/1995 | Young et al. | 128/634 |

FOREIGN PATENT DOCUMENTS

| 0 484 547 A1 | 5/1991 | European Pat. Off. |
| 0 575 737 A1 | 5/1993 | European Pat. Off. |
| 29 42 178 A1 | 10/1979 | Germany |
| WO 91/15151 | 4/1991 | WIPO |

OTHER PUBLICATIONS

Decker et al., "A Comparison of a New Perflectance Oximeter with the Hewlett–Packard Ear Oximeter," Biomedical Instrumentation & Technology, pp. 122–126, Mar./Apr. 1990.

"Trans–Esophageal Pacing", Pace, vol. 6, Jul.–Aug. 1983, p. 674.

"In Vivo Reflectance of Blood and Tissue as a Function of Light Wavelength", IEEE Transactions on Biomedical Engineering, vol. 37, No. 6, Jun. 1990, p. 632.

*Primary Examiner*—Jennifer Bahr
*Assistant Examiner*—Eric F. Winakur
*Attorney, Agent, or Firm*—Snell & Wilmer LLP

[57] ABSTRACT

A probe useful for invasively monitoring the oxygen saturation level of blood in the tissue walls of an anatomical canal generally includes a chassis with an electrical connector extending from the proximal end of the chassis and terminating at a plug configured for connection to a pulse oximeter box. The probe further includes an optics assembly configured to generate and transmit electrical signals that are indicative of the dynamic oxygen saturation level of blood in the wall tissue. The probe further includes a deployment device attached to the chassis for biasing the optics assembly into the tissue wall of the anatomical canal.

23 Claims, 8 Drawing Sheets

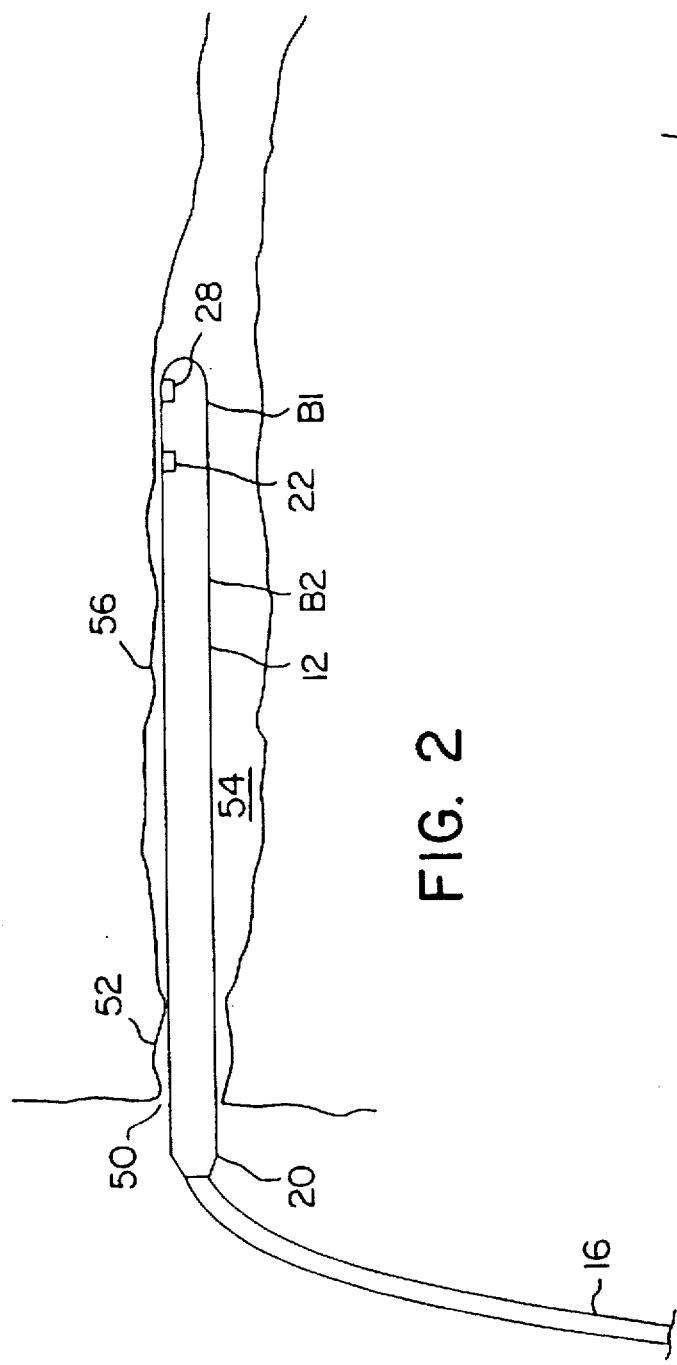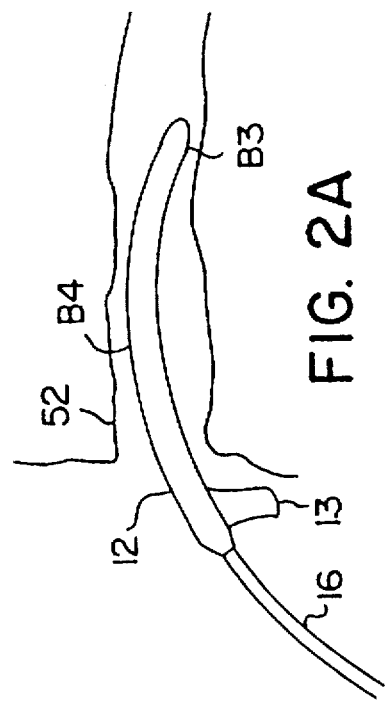

5,743,261

1

METHODS AND APPARATUS FOR THE INVASIVE USE OF OXIMETER PROBES

CROSS-REFERENCE TO RELATED APPLICATION

The present invention is a continuation-in-part of U.S. Ser. No. 08/163,052 filed Dec. 6, 1993, now U.S. Pat. No. 5,417,207 issued May 23, 1995.

TECHNICAL FIELD

The present invention relates, generally, to pulse oximetry, and more particularly to the invasive, in vivo use of oximeter probes in anatomical canals of humans and animals.

BACKGROUND OF THE INVENTION

Pulse oximetry, involving the continuous, non-invasive monitoring of oxygen saturation level in blood perfused tissue, is becoming an increasingly important mechanism for determining patient condition both during and following medical procedures. Indeed, the use of pulse oximeters has expanded in recent years to the point where they are now considered essential in the context of many surgical, emergency room, intensive care, and neonatal applications. The use of pulse oximetry is also expanding into the areas of out-patient surgery centers, oral maxillofacial surgery, home care, and in the veterinary environment.

Pulse oximetry typically involves the use of an oximeter probe (sensor) in contact with the patient. The sensor provides an electrical output signal to an oximeter box, which houses electronic circuitry used to process the electrical signal and generate human-readable indicia of various physiological parameters, including the patient's blood oxygen saturation level and pulse rate. Pulse oximetry systems are currently available from a number of manufacturers, including model no. N-200 manufactured by Nellcor of Chula Vista, Calif.

Non-invasive pulse oximeter probes have traditionally employed transmittance technology, whereby light is passed through a portion of the patient's blood perfused tissue and analyzed to determine the blood saturation level of the tissue. More particularly, traditional oximeter probes comprise an LED assembly and a photodetector assembly spaced apart from each other and mounted to a flexible substrate. This substrate is configured to be attached to a convex portion of the patient's anatomy, for example a finger, toe, ear and in the case of neonatal applications, to the ball of the foot. The oximeter probe may be conveniently attached to the patient by adhesive, a spring clip, Velcro, and the like. See, for example, Young, et al., U.S. Pat. No. 5,217,012 issued Jun. 8, 1993.

When properly attached to a patient, a transmittance oximeter probe is configured such that light emitted by the LED assembly passes through the patient's blood perfused tissue and is received by the photosensor assembly. The absorption characteristics of the transilluminated tissue are related to the oxygen saturation level of hemoglobin flowing through the tissue. Changes in the hemoglobin absorption characteristics influence the amount of light received by the photosensor, thus permitting the direct, non-invasive monitoring of arterial oxygen content. The photosensor assembly produces an output signal indicative of blood oxygen saturation level.

More recently, reflectance technology has been employed in the context of oximeter probes. Reflectance technology involves the use of an emitter assembly and a detector assembly mounted on a substrate and attached to the patient in an essentially co-planar fashion, for example on a patient's forehead or chest. When so mounted, light emitted by the emitter assembly passes through the patient's epidermis and is variously scattered and absorbed by the capillary and arterial beds, sweat glands, sebaceous glands, hair follicles, and the like beneath the patient's skin. During steady state operation of a reflectance probe, changes in the blood oxygen level of the blood perfused tissue proximate the sensor influence the amount of light received by the photosensor assembly in a manner analogous to transmission probes.

The theory of pulse oximetry, whether employed in the context of reflection or transmission sensing devices, is that the light received by the photosensor assembly and, hence, the blood oxygen level of the associated tissue, is a function of, inter alia, the relatively constant absorption characteristics of tissue, venus blood, and the like, as well as the variable absorption characteristics resulting from pulsations in arterial blood flow. Stated another way, the signal emitted by the photosensor assembly includes a DC component which is substantially independent of changes in blood oxygen saturation level, as well as a pulsatile AC component reflective of changes in blood oxygen saturation level.

In order to properly interpret changes in the oxygen saturation level of blood perfused tissue, a reasonably stable arterial pulsation is desired; indeed, an optical differencing measurement is typically made in accordance with this pulsation to determine the patient's pulse rate and oxygen saturation level. Moreover, a certain minimum threshold level of perfusion is generally needed in order to accurately detect changes in blood oxygen saturation level.

While suitable perfusion often exists at extremity sites (e.g., fingers, toes), a number of circumstances inhibit proper perfusion. For example, even in healthy pediatric and neonatal patients, lower mean arterial pressure and smaller arterial pathways inherently restrict the level of perfusion available for interrogation, particularly at the extremities. Moreover, in adults, conditions of critical illness, lowered body temperature, shock, trauma, burn, and other circumstances limit perfusion level as well as the ability to properly interface a sensor to a particular anatomical site. Accordingly, in many risk groups, conventional pulse oximeters are poorly adapted to situations wherein they are most needed. Moreover, many environmental factors, including the effects of changes in ambient light, humidity, and patient movement limit the practical utility of conventional oximeter sensors.

There thus exists a long felt need for an alternate site and monitoring configuration that positively addresses the limitations of presently known sensors.

SUMMARY OF THE INVENTION

An invasive electro-optical sensor probe according to the present invention addresses many of the shortcomings of the prior art.

In accordance with one aspect of the present invention, an oximeter probe is suitably disposed at a distal end of an elongated, flexible chassis. The chassis is suitably configured for insertion into an anatomical canal, for example in the esophagus, rectum, or vaginal cavity of a human patient. Inasmuch as the hemoglobin oxygen transport mechanism is substantially identical for all mammals as well as many other animals, the reflectance probe in accordance with the present invention, may also be suitably employed in the context of many veterinary applications. This is particularly advantageous inasmuch as many animals are poorly suited for conventional transmittance and reflectance probes due to the presence of hair, fur, and other complications associated with skin thickness, pigmentation, and the like.

In accordance with a further aspect of the present invention, the emitter assembly and detector assembly may be optimally configured for use in the context of an anatomical cavity, for example proximate a mucus membrane, thereby reducing many complications associated with externally attached probes, for example, complications due to ambient light, patient movement, pigmentation, undesirable reflectance due to epidermal skin layers, and the like. Inasmuch as esophageal and rectal sensing sites are typically rich arterial bed sites and, hence, good locations for core oxygen saturation measurements, a greater spacing between the emitter and detector assemblies may be employed and/or a lower signal source may be applied to the emitter assembly while still achieving satisfactory and even superior quality output signals from the detector assembly.

In accordance with yet a further aspect of the present invention, the emitter and detector assemblies are suitably configured for use in the context of an anatomical canal and are biased against the tissue walls of the cavity. Such a configuration advantageously ensures that a desired optical path through the vascular bed of the tissue is obtained.

In accordance with still a further aspect of the present invention, the emitter and detector assemblies are suitably configured to isolate vascular signals within the tissue wall of the anatomical canal in which the probe is used.

In accordance with a further aspect of the present invention, the reflectance oximeter sensor may be used in conjunction with existing invasive medical apparatus, for example in the context of an endotracheal tube or a core body temperature probe; in such context, the emitter and detector assemblies may be suitably "piggybacked" onto or integrated with the endotracheal tube, temperature probe, and other such assemblies.

BRIEF DESCRIPTION OF THE FIGURES

The present invention will be hereinafter described in conjunction with the appended drawing figures, wherein like designations denote like elements, and:

FIG. 2 shows an exemplary probe inserted into an anatomical canal;

FIG. 2A shows an alternate configuration of the sensor of FIG. 2;

DETAILED DESCRIPTION OF PREFERRED EXEMPLARY EMBODIMENTS

Figure 1:
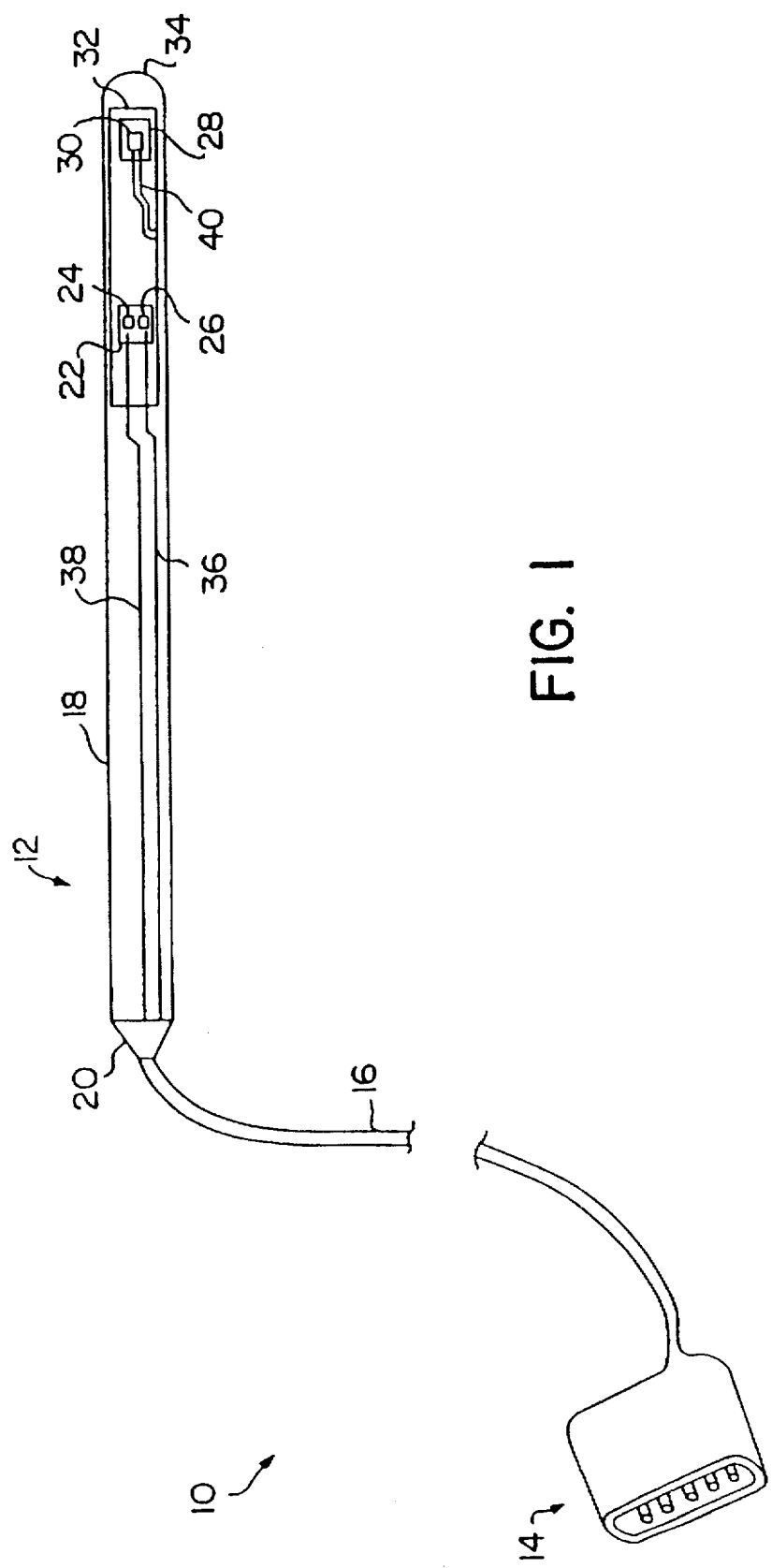
FIG. 1 is a top view of a reflectance probe in accordance with the present invention.

Referring now to FIG. 1, an exemplary probe assembly 10 suitably comprises a chassis 12, a plug 14, and an electrical cable 16 connecting chassis 12 with plug 14. Plug 14 is illustratively configured for attachment to an oximeter box or other output assembly configured to display indicia of, inter alia, blood oxygen saturation level, pulse rate, and the like.

In accordance with a preferred embodiment of the present invention, chassis 12 is suitably configured to be removably inserted into an anatomical canal, for example, the esophagus or rectum of a human or animal. Accordingly, cable 16 may be advantageously attached to chassis 12 via a junction 20 which securely grasps cable 16. Moreover, in accordance with a particularly preferred exemplary embodiment, junction 20 and chassis 12 are advantageously of integral, unitary construction to ensure that the device may be completely removed, intact, from an anatomical canal.

In accordance with a further aspect of the present invention, chassis 12 is suitably made from any desired biocompatible material, for example, polyurethane, polyethylene, PVC, PTFE, and/or the like. In accordance with a further aspect of the present invention, chassis 12 may be rigid, semi-rigid, flexible, or any desired degree of resiliency, depending on the particular application. For example, if the device is configured for use within the rectum of a large animal, e.g., a horse, a higher degree of rigidity may be appropriate. On the other hand, if the device is to be used in the esophagus or trachea in a child or an infant, a high degree of flexibility may be appropriate. Moreover, chassis 12 may comprise any suitable shape in cross-section, depending on, inter alia, the geometry of the anatomical canal within which the device is to be inserted, the geometry and topology of the optics associated with the device, and the use of the device in conjunction with other medical apparatus, as discussed in greater detail below. In this regard, chassis 12 may be suitably circular, elliptical, semispherical, arcuate, or substantially flat in cross-section, as desired.

With continued reference to FIG. 1, sensor 10 further comprises an emitter assembly 22 and a detector assembly 28 mounted on the surface of or within chassis 12. More particularly, emitter assembly 22 suitably comprises one or more light-emitting diodes (LEDs); in the illustrated embodiment, emitter assembly 22 comprises a first LED 24 having a wire 38 connected thereto, and a second LED 26 having a wire 36 connected thereto. Further, said LEDS are electrically connected in parallel such that electrical current flowing in one direction through wires 36 and 38 will cause the first LED 24 to operate, and electric current flowing in the opposite direction will cause first LED 24 to cease operation and cause the second LED 26 to operate. Respective wires 36, 38 extend along the length of chassis 12, through junction 20, and into cable 16.

Detector assembly 28 suitably comprises a detector 30 configured to sense at least a portion of the output of emitter 22. In the illustrated embodiment, detector 30 comprises a photodetector, for example, a photodiode. A suitable pair of wires 40 interconnects detector 30 and plug 14 via cable 16.

With continued reference to FIG. 1, emitter assembly 22 and detector assembly 28 are suitably mounted to a spacer 32 to thereby maintain a constant spacing between the emitter and detector assemblies.

Emitter assembly 22 and detector assembly 28 are suitably mounted on the surface of or within chassis 12 in a manner which permits light emitted by the emitter assembly to pass through the blood perfused tissue interrogated by sensor 10 and to be received by detector assembly 28. If the emitter and detector assemblies are to be mounted within chassis 12, at least the distal portion of chassis 12 proximate the emitter and detector assemblies advantageously comprises a transmissive material to permit light to pass therethrough in the vicinity of emitter 22 and detector 28. Alternatively, emitter assembly 22 and detector assembly 28 may be mounted on the surface of or integral with the outer wall of chassis 12. In accordance with an alternate embodiment of the present invention, the emitter and detector may suitably be mounted within or otherwise integral with various other medical apparatus, for example, a temperature probe, an endotracheal tube, catheter, and the like.

For veterinary applications, and particularly for esophageal and rectal applications involving large animals, chassis 12 may suitably be in the range of 2 to 24 inches long, and preferably in the range to 4 to 12 inches long, and most preferably 5 to 10 inches long. Chassis 12 may also suitably exhibit a cross-sectional dimension in the range of 0.25 to 1.5 inches and most preferably in the range of 0.3 to 0.8 inches. For applications involving smaller animals, chassis 12 may be on the order of 2 to 12 inches in length, and most preferably in the range of 4 to 5 inches with a cross-sectional dimension in the range of 0.25 to 0.75 inches and most preferably in the range 0.3 to 0.5 inches In this regard, chassis 12 may exhibit any suitable cross-section geometry, e.g., flat, circular, and the like, as discussed above. Moreover, in both veterinary and human applications, chassis 12 may comprise any suitable longitudinal shape, whether straight, curved, angled, arced, and the like, to permit optimal placement of the optical components of the device.

In accordance with a preferred embodiment of device 10 wherein chassis 12 is configured for insertion into a human rectum, chassis 12 is suitably in the range of 3 to 10 inches long, and preferably in the range of 4 to 8 inches long, and most preferably in the range of 5 to 7 inches long. For such rectal applications, chassis 12 may suitably exhibit a circular or elliptical cross-sectional geometry, having a cross-sectional dimension in the range of 0.3 to 1.0 inches, and most preferably in the range of 0.4 to 0.7 inches. For applications involving children and infants, chassis 12 is suitably 3 to 7 inches long, and preferably 4 to 6 inches long, exhibiting a cross-sectional dimension on the order of 0.25 to 0.5 inches, and most preferably 0.35 inches.

In an alternate preferred embodiment, chassis 12 may be configured for insertion into a human esophagus. In this embodiment, chassis 12 suitably is 6 to 16 inches long, and preferably 8 to 14 inches long, and most preferably 9 to 12 inches long. For esophageal applications, although chassis 12 may exhibit any suitable cross-sectional geometry, the present inventors have determined that a substantially flat, elliptical, or arcuate cross-sectional geometry may facilitate positioning the optical elements within the esophageal canal.

Referring now to FIG. 2, chassis 12 is suitably configured for insertion into an anatomical canal 50, for example, the esophagus or a rectum of a human or animal. More particularly, canal 50 suitably comprises an opening 52, which may comprise a sphincter, a canal passageway 54, and a canal wall 56. In accordance with one aspect of the present invention, chassis 12 is desirably configured such that emitter assembly 22 and detector assembly 28 may be positioned proximate wall 56, suitably in intimate contact therewith.

In accordance with a further aspect of the invention, chassis 12 is suitably configured such that it may be inserted within canal 50 to any desired length, such that junction 20 remains outside the canal. In this regard, it may be desirable to equip chassis 12 with wings (not shown) or other structure in the vicinity of junction 20 to prevent the device from being inserted within the canal beyond junction 20.

Figure 3:
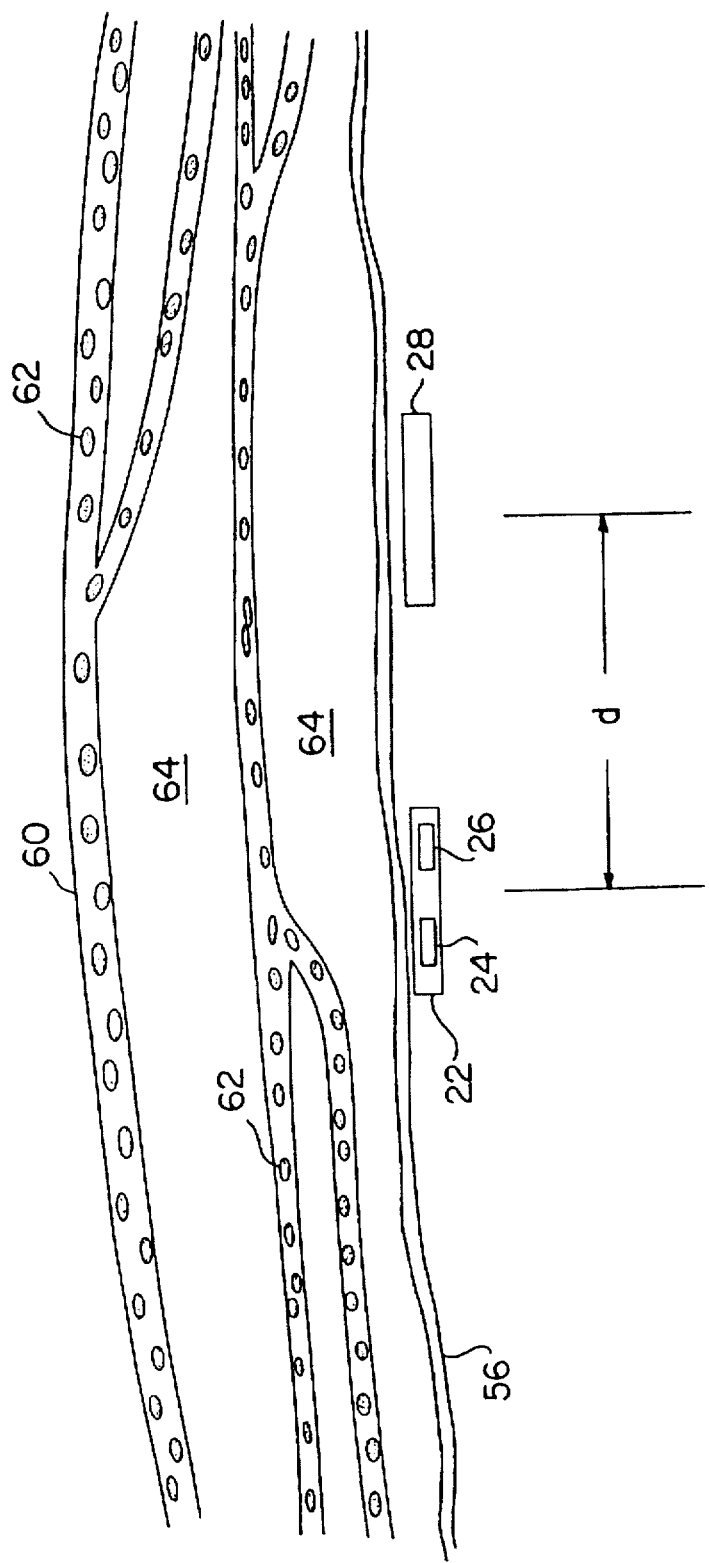
FIG. 3 is a schematic representation of an emitter and detector assembly disposed in situ, and showing the subdermal arterial hemoglobin transport mechanism for a typical patient.

Referring now to FIG. 3, canal wall 56 suitably comprises a mucus membrane, with dermal and subdermal tissue 64 laying beneath the surface of wall 56. An arterial bed comprising various arteries 60 suitably extends throughout the subdermal region proximate wall 56. The arterial blood carried by arteries 60 includes, among other things, blood cells (not shown) and particulate hemoglobin 62.

Pulse oximeters employ the principal of differential light absorption to determine the level of oxygen saturation of hemoglobin in arterial blood. In particular, the light absorption characteristics of oxyhemoglobin are very different from the light absorption characteristics of deoxyhemoglobin. Furthermore, the extinction coefficient for a hemoglobin solution is related to the absorption coefficient of the hemoglobin divided by the concentration. The absorption coefficient of a blood sample, which can be determined based on its oxygenation level and the extinction coefficients associated with the various components of the blood sample, is dependent upon both the wavelength of light used to interrogate the blood sample, as well as the oxygen saturation level of the blood sample.

With continued reference to FIG. 3, light emitted by emitter assembly 22, which is suitably proximate to or in intimate contact with wall 56, passes through tissue 64, arteries 60, and hemoglobin 62. In so doing, a portion of the light is absorbed by these constituents, and some of the light is scattered by these same constituents. The amount of scattered light which is received by detector assembly 28 is a function of, inter alia, the spacing D between emitter 22 and receptor 28, the size and configuration of emitter 22 and detector 28, and the oxygen saturation level of hemoglobin 62 with the arterial bed proximate the probe. By monitoring a characteristic of the output of detector circuit 28 (e.g., voltage, typically current), the oxygen saturation level of the blood perfused tissue may be dynamically and continuously ascertained.

In accordance with a particularly preferred embodiment, two wavelengths of light, for example red and infra-red, are desirably emitted by first LED 24 and second LED 26, respectively. As stated above, the light absorption characteristics of oxygenated hemoglobin differ markedly from the absorption characteristics of deoxygenated hemoglobin; at the same time, the difference in absorption characteristics of oxygenated and deoxygenated hemoglobin is also a function of wavelength. In accordance with a preferred embodiment of the invention, the light emitted from emitter 22 is suitably chopped, such that emitter 24 is turned on for a predetermined period, then turned off for a predetermined period to allow the electronics to settle; thereafter, emitter 26 is energized for a predetermined period and thereafter turned off for a predetermined period, and the cycle is repeated. In this way, detector 28 ultimately receives a portion of light emitted at the first wavelength, and thereafter receives a portion of the light emitted at the second wavelength, in a repetitive fashion. As is known in the art, by monitoring two different wavelengths of light, the system can compensate for fluctuations in the level of light received by detector 28 which are unrelated to the level of oxygen saturation of the underlying hemoglobin. See, for example, *Pulse Oximeters*, 185–189 *Health Devices*, Vol. 18, No. 6, (June, 1989); Cui and Ostrander "In Vivo Reflectance On Blood And Tissue As A Function Of Light Wavelength", 630–639, *IEEE Transactions On Biomedical Engineering*, Vol. 37, No. 6 (June, 1990); and Decker, Dickensheets, Arnold, Cheung and Strohl, "A Comparison Of New Reflectance Oximeter With the Hewlett-Packard Oximeter", 122–126, *Biomedical Instrumentation And Technology*, (March/April, 1990).

In accordance with one aspect of the present invention, chassis 12 may be configured for insertion into an anatomical canal for example the esophagus or rectum of an animal or human. It is notable that many such cavities comprise a mucus membrane wall, a rich artsrial bed site. Moreover, by employing a mucus membrane or similar anatomical sight for interrogation, many of the problems associated with non-invasive sensing are eliminated or reduced. For example, light reflectance from the surface of the epidermis is substantially eliminated at a mucus membrane site. In addition, various effects of external light are eliminated, inasmuch as internal anatomical cavities are typically devoid of ambient light. In addition, internal body cavities are often free of hair, fur, fingernails, toenails, cartilage, scar tissue, and many other factors which influence the ability to efficiently pass light through an arterial bed.

Thus, in accordance with a further aspect of the invention, it may be possible to manipulate chassis 12 to thereby optimally position the optics with respect to the cavity wall. For example, chassis 12 may be rotated about its longitudinal axis until a robust, stable output is achieved. In addition, it may be desirable to incorporate a balloon, analogous to balloons employed in balloon angioplasty, into chassis 12. More particularly and with momentary reference to FIG. 2, a small balloon may be placed at any point along chassis 12, for example at one of respective points B1 or B2 on the opposite side of chassis 12 from the optical components. Upon inserting chassis 12 into the anatomical cavity, the balloons may be inflated slightly to thereby bias emitter 22 and detector 28 against the cavity wall.

In accordance with an alternate embodiment of the present invention, chassis 12 may suitably be substantially flat or, alternatively, have a first cross-sectional dimension which is significantly greater than a second transverse cross-sectional dimension (e.g., an ellipsoid), such that chassis 12 is substantially self-aligning within a body cavity. In this regard, it may also be desirable to place a first emitter assembly and a first detector assembly on one side of the chassis, and a second emitter assembly and a second detector assembly on the opposing side of the distal end of the same chassis, such that light is emitted in opposite directions, i.e., against two opposing walls of the cavity. In accordance with such an embodiment, the output signals from the first and second detector assemblies may be monitored such that the system selects the most desirable signal for display based on, inter alia, signal-to-noise ratio, signal strength, signal stability, and the like.

The foregoing embodiment employing redundant optical circuitry may be particularly advantageous in situations where the anatomical canal may be partially obstructed. For example, in a veterinary application involving horses, often a portion of the rectal canal may be obstructed by fecal matter. When chassis 12 is inserted into the rectal canal, it may become lodged between a canal wall (mucus membrane) and the fecal matter. By monitoring the signal derived from the cavity wall and comparing it to the signal derived from the electronics proximate the fecal matter, it may be possible to utilize the signal from the optoelectronics proximate the cavity wall and disregard the signal from the optics proximate the fecal matter.

In accordance with a further embodiment wherein chassis 12 may be employed in the birth canal or womb of a human or animal (e.g., by inserting the device through the vagina), it may be particularly desirable to employ redundant electronics to sense one or both of the oxygen saturation level of the mother, as well as that of the baby in the birth canal. Additionally, chassis 12 may be employed in a human or animal inner ear.

In accordance with a further aspect of the invention, chassis 12 may assume any desired shape to permit optimal placement of the electronics proximate the internal cavity wall. For example chassis 12 may suitably be of any desired shape, for example, "banana" shaped; such a configuration would tend to bias the optoelectronics against the cavity wall, for example, by disposing the optoelectronics at point B3 or B4 of chassis 12 (see FIG. 2A). With continued reference to FIG. 2A, it may also be desirable to incorporate a suitable selectively controllable spring mechanism into chassis 12, such that the arc may be increased or decreased in situ, as desired, to achieve optimal placement of the optoelectronics with respect to the cavity wall.

In accordance with yet a further aspect of the present invention, the oximetry optoelectronics may be suitably incorporated into other medical apparatus, including an endotracheal tube, temperature probe, and the like. For those situations in which invasive treatment is required, i.e., the use of an endotracheal tube or a core body temperature probe, pulse oximetry data may be obtained in accordance with the present invention without the need to insert additional invasive apparatus into the patent.

In accordance with yet a further aspect of the invention, a suitable handle 13 or other manual or visual indicia (See FIG. 2A) may be incorporated into the proximal end of chassis 12. Handle 13 permits the physician to dynamically control the degree of axial insertion of the device as well as the rotational position of the device to ensure optimal placement of the optoelectronics. In this regard, handle 13 may be any desired distance from the optoelectronics. By monitoring the position of handle 13 with respect to opening 52 of the anatomical cavity, the precise position of the optoelectronics within the cavity may be unambiguously inferred.

In accordance with yet a further aspect of the invention, various biocompatible lubricants may be employed in conjunction with device 12 to facilitate insertion and removal of the device. Since these lubricants are generally optically transparent at wavelengths of interest and present a DC or steady state attenuation of light only, they generally do not interfere with accurate oxygen readings. Moreover, for those embodiments wherein a controllable spring mechanism is used to control the arc associated with chassis 12 (FIG. 2A), or in those embodiments in which a balloon is employed to position the optoelectronics, these features may also be employed to ensure that chassis 12 remains in place for extended periods of time.

In accordance with a further aspect of the invention, any convenient wavelength or pair of wavelengths may be employed in conjunction with emitter circuit 22. In accordance with a particularly preferred embodiment, first LED 24 suitably emits light in the range of 540 to 690 nanometers, and preferably in the range of 650 to 670 nanometers, and most preferably 660 plus or minus 5 nanometers. Second LED 26 suitably emits light in the range of 880 to 940 nanometers, and preferably in the range of 890 to 920 nanometers, and most preferably 905 plus or minus 10 nanometers.

In accordance with a further aspect of the invention, the distance D (FIG. 3) between the emitter and the detector assembly is suitably in the range of 0.5 to 5 centimeters, and preferably in the range of 1.5 to 2 centimeters. In certain high sensitivity applications, it may be desirable to slidably mount one or both of the emitter and detector assemblies to permit controlled variation of Distance D during use. In this regard, both the signal strength applied to the emitter circuit and the distance D may be manipulated to achieve optimum data performance.

In accordance with a further aspect of the present invention, as previously briefly mentioned above, chassis 12 of probe assembly 10 may be suitably provided with devices or other implements useful in biasing and thereby maintaining emitter 22 and detector 28 against the cavity wall. In particular, the present inventors have found that optimal oximetric readings can be best obtained by coupling the sensor with the cavity tissue lining, thereby creating a desired optical path through the vascular bed of the tissue. Accordingly, chassis 12 can be suitably configured with a deployment device to bias emitter 22 and detector 28 against and/or into the tissue of an anatomical cavity. Preferred exemplary embodiments of the invention incorporating such deployment devices may utilize inflatabassists. How spring configurations and/or other mechanical assists. However, it should be appreciated that deployment devices useful in the context of the present invention are not limited to these exemplary embodiments.

Figure 4:
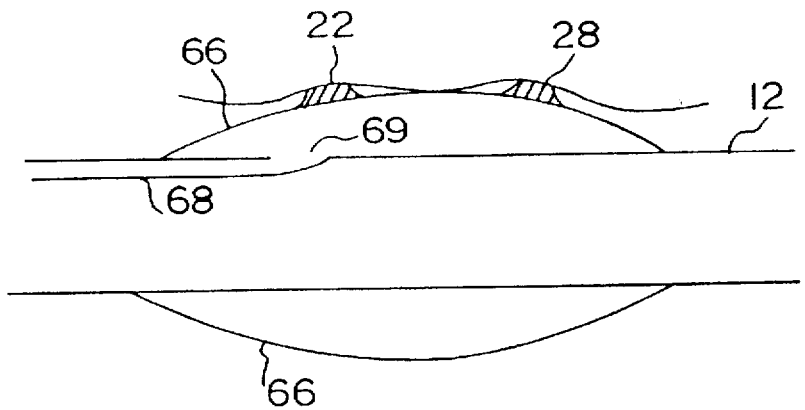
FIG. 4 shows a cross-sectional view of a portion of a further embodiment of a probe in accordance with the present invention utilizing an inflatable balloon biasing device.

Referring now to FIG. 4, a first exemplary embodiment of a deployment device useful in the context of the present invention comprises an inflatable balloon 66. In this illustrated embodiment inflatable balloon 66 is suitably attached to probe chassis 12. Emitter 22 and detector 28 are firmly affixed to an outer surface of balloon 66. Preferably, emitter 22 and detector 28 are attached to balloon 66 in any conventional manner, such as through the use of adhesives or the like. For example, UV cure adhesives and the like may be employed. Balloon 66 is suitably attached to chassis 12 in any conventional manner. In accordance with one aspect of the present invention, balloon 66 is suitably molded to the exterior surface of chassis 12. Balloon 66 may comprise any conventional material, for example, latex. In the case where the probe assembly 10 is used on humans as an esophageal probe, balloon 66 may advantageously comprise an endotracheal cuff (not shown) and be attached to chassis 12 in a conventional manner.

With continued reference to FIG. 4, balloon 66 is suitably inflated, such as by pumping air down the balloon inflation channel (tube) 68 into balloon 66. When balloon 66 is so inflated, emitter 22 and detector 28 are suitably pushed outward away from chassis 12 and biased against and into the anatomical cavity wall. Channel 68 communicates with balloon 66 through at least one port 69 extending through chassis 12. Air may then be pumped through channel 68 to balloon 66 using conventional monitors to control pressure, inflation rate, and/or the site of the inflated balloon. Axial and translational movement within the anatomical cavity is thus substantially inhibited for chassis, and, hence, the probe optics. Moreover, emitter 22 and 28 are suitably deployed into cavity wall 56 to thereby establish intimate optical contact therewith. It should be appreciated that while channel 68 is shown as extending along a wall of chassis 12, other orientations may be employed.

Figure 5:
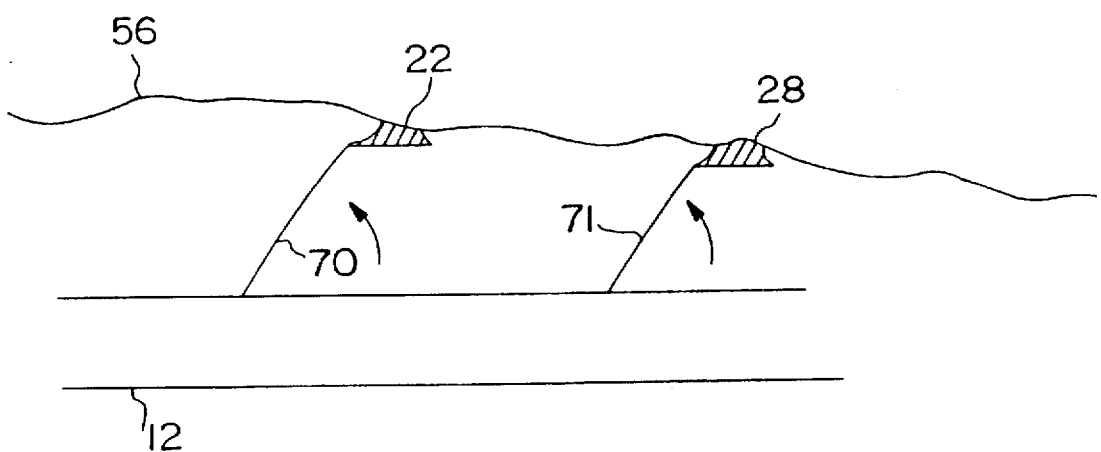
FIG. 5 shows a cross-sectional view of a portion of a further embodiment of a probe in accordance with the present invention within an anatomical canal utilizing an alternate biasing device.

In accordance with a further exemplary embodiment, a deployment device useful in connection with oximeter probes of the present invention may comprise a spring. With reference to FIG. 5, emitter 22 and detector 28 are advantageously attached to respective springs 70 and 71 such as through the use of any suitable adhesive or fastening mechanisms. Alternatively, the base of emitter 22 and detector 28 may be mechanically extruded onto or in conjunction with springs 70 and 71 during manufacture. As shown, springs 70 and 71 may be used to bias and deploy emitter 22 and detector 28 into anatomical cavity wall 56. In this illustrated embodiment, springs 70 and 71 suitably comprise leaf or other springs securely affixed to chassis 12 and also to emitter 22 and detector 28, respectively. Preferably, springs 70 and 71 are of a suitable size and dimension to advantageously bias emitter 22 and detector 28 into wall 56, and thus the size and dimension of springs 70 and 71 will depend upon the particular application. In the case where the probe assembly is used as an esophageal probe, springs 70 and 71 are suitably configured to deploy emitter 22 and detector 28 from chassis 12, typically having a diameter on the order of about 3 mm, into the esophageal wall lining which may be as Marge as about 3 cm for a fully distended esophagus. Thus, the springs are advantageously configured to accomodate radial extension in the range of 1 mm to 5 cm, and most preferably about 3 cm.

While springs 70 and 71 are illustrated as leaf springs, it should be appreciated that coil or other similar springs which can be attached to chassis 12. Springs 70 and 71 may suitably comprise any flexible material, such as metal, plastic, rubber, thermoplastic and/or the like.

Figure 6:
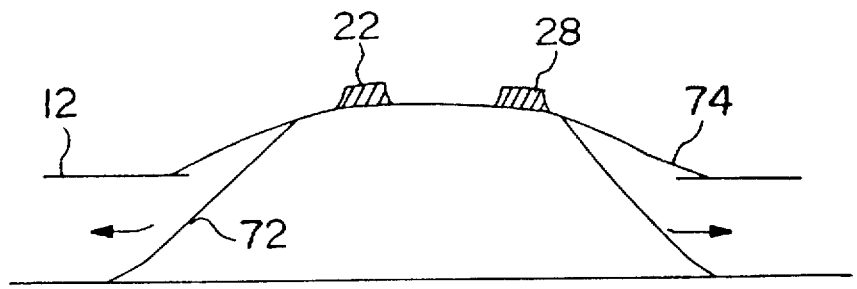
FIG. 6 shows a cross-sectional view of a portion of still a further embodiment of a probe in accordance with the present invention utilizing a further alternate biasing device.

In accordance with a further exemplary embodiment of the present invention, and with reference to FIG. 6, a deployment device useful in connection with oximeter probe assemblies of the present invention may suitably comprise a single retractable leaf spring 72 or the like. As shown in FIG. 6, spring 72 is preferably connected to a wall of chassis 12 and a flexible substrate 74 suitably affixed to an opposing wall of chassis 12. Substrate 74 may comprise a polymeric or metallic material, or any other material providing sufficient flexibility to deploy the optoelectronics into cavity wall 56. Emitter 22 and detector 28 are suitably attached to the outer surface of substrate 74 such that when spring 72 actuated; it expands substrate 74 away from the outer surface of chassis 12 and biases emitter 22 and detector 28 against cavity wall 56. In connection with this aspect of the present invention, the probe assembly may be further provided with a device suitably configured to activate deployment device 72. For example, as the probe assembly is inserted into the anatomical cavity, it may be desirable to have spring 72 in a position where it does not engage substrate 74, and then, when the probe is suitably positioned within the cavity, cause device 72 to engage substrate 74 thus causing emitter 22 and detector 28 to be deployed. Any convenient mechanism may be used for this purpose, such as a push rod or the like.

Figure 10:
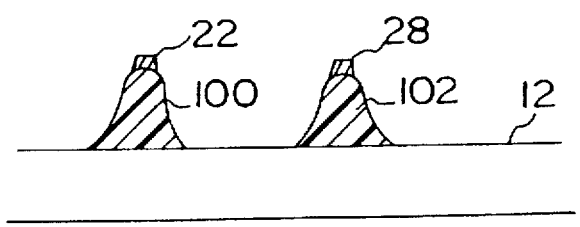
FIGS. 10 and 10A show cross-sectional views of a portion of yet another embodiment of a probe in accordance with the present invention.
Figure 10A:
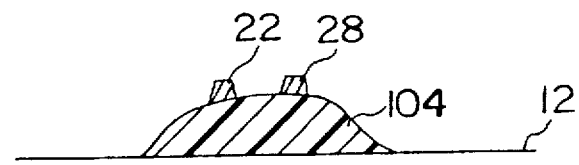

It should be appreciated that other deployment devices may be suitably used in connection with the present invention. For example, a single retractable leaf spring similar to spring 72 may be suitably attached to the external surface of chassis 12 and emitter 22 and detector 28 suitably attached thereto. Alternatively, in place of flexible springs or the like, the outer surface of tube 12 may simply be built up in the form of a single protuberance 104 (see FIG. 10A) or respective multiple protuberances 100 and 102 (see FIG. 10). In accordance with this aspect of the present invention, protuberances 100, 102 and 104 may be formed in any suitable fashion such as by molding silicon or other polymeric materials to the outer surface of chassis 12. As shown in FIGS. 10 and 10A, the electro-optical components associated with the probe assembly, namely emitter 22 and detector 28, may be advantageously affixed to such protuberances. While caution must be observed so that the overall dimension of probe assembly 10 in the region of the optoelectrical components is not excessively oversized, enlarging the dimension of chassis 12 to sufficiently deploy the electro-optical components into contact with cavity wall 56 should not have deleterious effects on cavity wall 56.

In general, in accordance with this aspect of the present invention, the electro-optical components utilized in connection with the subject probe are suitably attached to chassis 12 in a manner which enables them to be advantageously deployed into and/or against the wall of the anatomical cavity into which the probe is inserted. While various modifications may be made which are within the scope of the present invention, the illustrated embodiments shown herein offer low cost improvements over prior esophageal probes in that oximetry measurements can be efficiently and reliably obtained through use of a relatively low cost probe. Moreover, the deployment devices utilized in connection with the subject probes of the present invention, preferably offer the further advantage of minimizing movement of cavity 12 during interrogation.

Figure 7:
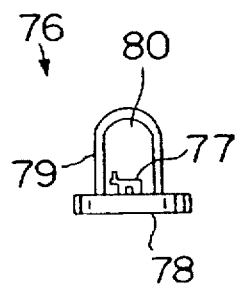
FIG. 7 is a side view of a preferred configuration of a sensor optical coupler useful in conjunction with a probe in accordance with the present invention.

In accordance with still a further aspect of the present invention shown in FIG. 7, a sensor optical coupler 76 may be advantageously configured to house the electro-optical components, namely emitter 22 and detector 28. Coupler 76 is suitably configured to permit effective optical communication between the electro-optical components, namely emitter 22 and detector 28, or similar electro-optical components.

With continued reference to FIG. 7, a coupler (button) 76 preferably comprises an electro-optical component 77 suitably affixed to a base (substrate) 78. A sleeve 79 is suitably attached to base 78 and configured to surround at least a portion of component 77. Sleeve 79 is suitably covered by a top 80 preferably exhibiting a substantially dome shaped profile. In accordance with a preferred aspect of the present invention, an optically opaque material, such as polymeric materials having optically opaque characteristics, e.g., black polyolethin and the like, may be utilized to form sleeve 79. On the other hand, top 80 preferably comprises any material having suitable optically, transmissive properties, to permit light to pass through top 80. Sleeve 79, top 80, and base 78 are suitably secured together by any convenient mechanism, such as UV cure optical grade adhesives, epoxies, acrylics, sorcones and/or the like.

Preferably, coupler 76 has a substantially cylindrical shape (see FIG. 7B) which provides a suitable housing for electro-optical component 77. In this regard, it should be appreciated that component 77 may comprise either LEDs 24, 26 (FIG. 1) used in emitter 22, or photodiode 30 (FIG. 1) used in detector 28.

Sleeve 79 and lens 80 cooperate to generally displace the anatomical fluids within the cavity in the region of component 77, thereby providing more direct contact between component 77 and the cavity wall, e.g., wall 56. Preferably, sleeve 79 and lens 80 cooperate to provide an optical contact region 81. For example, with reference to FIG. 7A, region 81 may advantageously comprise top 80 positioned at the top of sleeve 79. Alternatively, and with reference to FIG. 7B, region 81 may be formed in a side wall of the substantially cylindrical button 76A as a portion of sleeve 79.

In accordance with an aspect of this embodiment of the present invention, button 76 can be formed into substrate 78, or preferably directly onto a portion of probe chassis 12 or any deployment device used in connection therewith. Through use of such a probe, assembly, reliable oximetric measurements can be obtained because inter alia the measurement site is near core body organs. However, because of the close location of these organs and the lack of pigmentation in anatomical cavity walls, the oximetry signal may be influenced by nearby vascular sources, and thus potentially require that additional interpretation methods be employed to arrive at the appropriate determination of cavity tissue arterial oxygen saturation. While proper placement of the electro-optical components tends to avoid these difficulties, in accordance with a further embodiment of the present invention, electro-optical components are suitably positioned such that the optical path traverses only the cavity tissue and other vascular signals are substantially avoided.

Figure 7A:
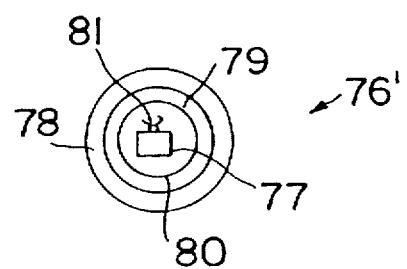
FIG. 7A is a top view of the coupler of FIG. 7.
Figure 7B:
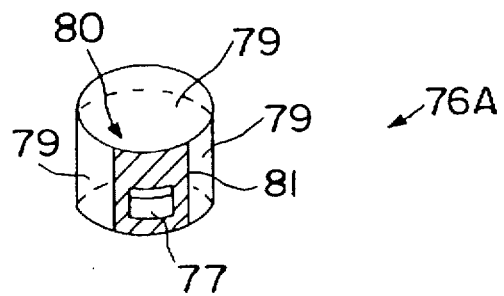
FIG. 7B is a perspective view of an alternate embodiment of a coupler useful in connection with a probe in accordance with the present invention.
Figure 8:
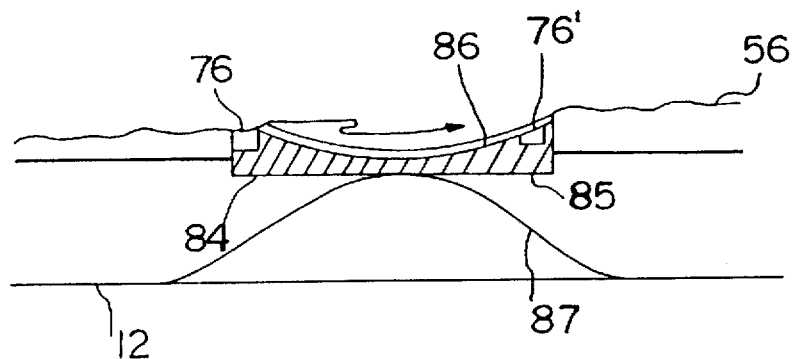
FIG. 8 shows a cross-sectional view of a portion of yet another embodiment of a probe within an anatomical canal in accordance with the present invention utilizing an alternate sensor.

For example, and with reference now to FIG. 8, respective optical couplers 76, 76' can be suitably affixed to a mounting platform 84. In accordance with this embodiment, optical coupler 76 suitably comprises respective LEDs similar to LEDs 24 and 26 (FIG. 1) as used in emitter 22; optical coupler 76' suitably comprises a photodiode similar to photodiode 30 (FIG. 1) as used in detector 28. In this illustrated embodiment, surface 84 preferably comprises a first surface 85 and a second surface 86. Preferably, couplers 76 and 76A are mounted in surface 86 which, as shown, is optimally configured to exhibit a concave profile. Preferably, a deployment member 87 is suitably attached to surface 85 of platform 84. While any deployment device may be used, in the illustrated embodiment member 87 is suitably configured in a fashion similar to spring 72. In accordance with this embodiment, couplers 76 and 76 are provided with an optically transmissive top, such as shown in FIGS. 7 and 7A, and in operation are biased into cavity wall 56 such that wall 56 tends to conform to the configuration of platform 84. In this manner, the signal from coupler 76 to coupler 76' tends to follow a substantially straight optical path transversing substantially only the recessed tissue of wall 56. Thus, the probe advantageously can be used in this manner to obtain measurements of the cavity lining arterial oxygen saturation without receiving unwanted signals from other internal vascular sources. Depending on the geometry of platform 84, and particularly of surface 86, a hybrid transmittance/reflectance optical system may be employed or, alternatively, a pure transmittance or pure reflectance system may be used.

Figure 9:
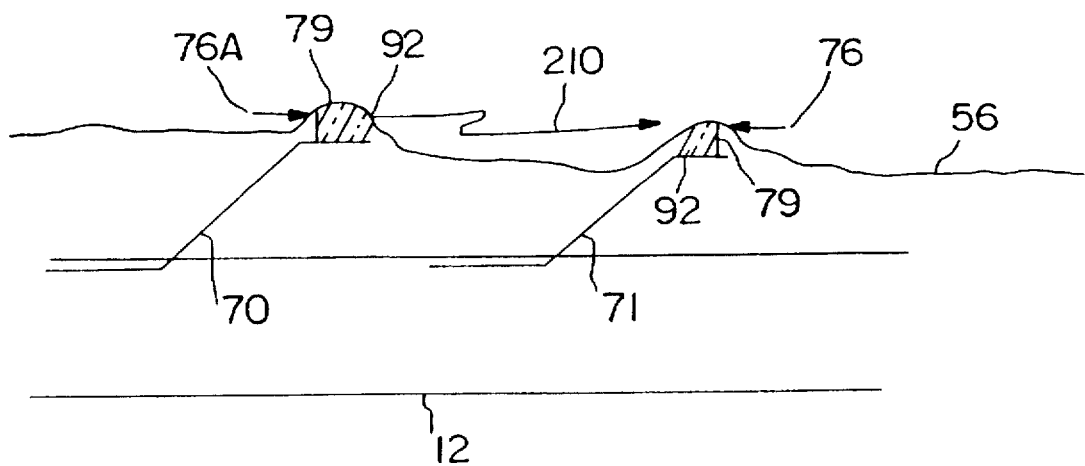
FIG. 9 shows a cross-sectional view of an alternate configuration of a probe in accordance with the present invention within an anatomical canal utilizing a further alternate sensor configuration employing the optical couplers of FIG. 7.

Referring now to FIG. 9, sensor optical couplers 76 and 76A (see FIG. 7B) can be used in connection with e.g., respective deployment devices 70 and 71 as shown in connection with FIG. 5. In accordance with this embodiment, sensor optical coupler 76A suitably comprises an emitter similar to emitter 22 and coupler 76 suitably comprises a detector similar to detector 28. As previously noted, optical couplers 76, 76A' preferably comprise an optically opaque casing 79 that surrounds the sensor (either an emitter or a detector) which casing defines an optical contact region 81, generally in the form of an optically clear window denominated 92 in FIG. 9. As shown, windows 92 are suitably arranged such that window 92 of coupler 76A is facing window 92 of optical coupler 76, thus tending to establish a substantially straight optical path 210 between couplers 76A and 76. In accordance with this embodiment, preferably couplers 76, 76 are affixed to one of the deployment devices discussed previously (e.g., springs), such that couplers 76, 76A' are forced into contact with cavity wall 56 deep enough that sufficient tissue overlies couplers 76 and 76A. As will be appreciated, the height of casing 79 can be adjusted as appropriate to allow for different configurations of window 92. For example, it may be desirable to configure the detector housing with a wider window than that which is provided in the emitter housing. For example, coupler 76 may have an optically opaque top and optically clear sides, or a window formed in the side which is wider than the corresponding window in coupler 76A.

In accordance with a further aspect of the present invention, coupler 76 can be suitably formed from an injection molded plastic or other polymeric material in any configuration which permits effective optical coupling between the electro-optical components of the probe assembly.

It will be understood that the foregoing description is of preferred exemplary embodiments of the invention, and that the invention is not limited to the specific forms shown. Various modifications may be made in the design and arrangement of the elements set forth herein without departing from the scope of the invention as expressed in the appended claims.

We claim:

1. A probe useful for invasively monitoring an oxygen saturation level of blood in at least one tissue wall of an esophagus, the probe comprising:
 a chassis having a proximal end and a distal end;
 an electrical connector extending from said proximal end of said chassis and terminating at a plug configured for connection to a pulse oximeter box;
 a reflectance optics assembly configured to generate and transmit electrical signals to said oximeter box, said signals being indicative of the oxygen saturation level of blood in the wall tissue; and
 a deployment device attached to said chassis and said reflectance optics assembly, said deployment device useful in urging said reflectance optics assembly into at least one tissue wall of the esophagus to aid in generation of said electrical signals.

2. The probe of claim 1 wherein said reflectance optics assembly comprises an emitter assembly and a detector assembly.

3. The probe of claim 2 wherein said deployment device comprises an inflatable balloon connected to said chassis, and wherein said emitter and detector assemblies are affixed to an external surface of said inflatable balloon.

4. The probe of claim 3 further comprising a balloon inflating tube operatively connected to said balloon and said chassis, said tube being configured to permit fluid to be passed into said balloon to inflate said balloon.

5. The probe of claim 2 wherein said deployment device comprises a spring assembly connected to said chassis.

6. The probe of claim 5 wherein said spring assembly comprises:
 a first spring mechanism, said emitter assembly being operatively connected to said first spring mechanism; and
 a second spring mechanism, said detector assembly being operatively connected to said second spring mechanism.

7. The probe of claim 6 wherein said deployment device further includes means for selectively controlling said first and second spring mechanisms to thereby control the placement of said emitter and detector assemblies along the length of said chassis.

8. The probe of claim 5 wherein said spring assembly comprises a single spring mechanism and said emitter and said detector assemblies are suitably affixed to said single spring mechanism.

9. The probe of claim 8 further comprising a substrate suitably connected to said single spring mechanism and said emitter and said detector assembly are affixed to said substrate.

10. The probe of claim 8 wherein said deployment device includes means for selectively controlling said spring mechanism to thereby control the placement of said emitter and detector assemblies along the length of said chassis.

11. The probe of claim 1 further comprising at least one sensor optical coupler, at least a portion of said reflectance optics assembly being contained within said coupler.

12. A method of invasively monitoring an oxygen saturation level of a blood perfused tissue of an esophagus, comprising the steps of:
 manually inserting a distal end of an oximeter probe comprising a chassis, a biasing device, an electro-optical emitter and an electro-optical detector into the esophagus;
 manually guiding said probe into said esophagus;
 manipulating said chassis and deploying said biasing device such that said emitter and said detector are sufficiently embedded into said blood perfused tissue;
 configuring an optical path between said emitter and said detector, such that said oximeter signal passes through said blood perfused tissue; and
 evaluating said signals from said detector to monitor the oxygen saturation level of said blood perfused tissue.

13. A probe useful for invasively monitoring an oxygen saturation level of blood in at least one tissue wall of an anatomical cavity, the probe comprising:
 a chassis having a proximal end and a distal end;
 an electrical connector extending from said proximal end of said chassis and terminating at a plug configured for connection to a pulse oximeter box;
 a reflectance optics assembly configured to generate and transmit electrical signals to said oximeter box, said signals being indicative of the oxygen saturation level of blood in the wall tissue;
 at least one sensor optical coupler containing at least a portion of said reflectance optics assembly; and
 a deployment device attached to said chassis and said reflectance optics assembly, said deployment device useful in urging said at least one sensor optical coupler into at least one tissue wall of the anatomical cavity.

14. The probe of claim 13, comprising at least two optical couplers, and wherein said reflectance optics assembly comprises at least an emitter assembly and a detector assembly, said emitter assembly being contained within a first of said optical couplers and said detector assembly being contained within a second of said optical couplers.

15. The probe of claim 14 wherein said first and second couplers comprise a housing having substantially cylindrical side walls and a substantially domed top.

16. The probe of claim 15 wherein said side walls of said first and second couplers are substantially optically opaque and said top of said couplers is formed of a substantially optically transmissive material.

17. The probe of claim 15 wherein said top and a first portion of said side walls of said first optical coupler is formed of an optically opaque material, and a second portion of said side walls of said first optical coupler is formed of an optically transmissive material.

18. The probe of claim 17 wherein said top and a first portion of said side walls of said second optical coupler is formed of an optically opaque material, and a second portion of said side walls of said second optical coupler is formed of an optically transmissive material.

19. The probe of claim 18 wherein said second portion of said second coupler side wall is of a larger dimension than said second portion of said first coupler side wall.

20. The probe of claim 15 wherein said first and second couplers are suitably mounted to a mounting platform, said mounting platform operatively connected to said chassis.

21. The probe of claim 20 wherein said deployment device is interposed between said platform and said chassis.

22. A probe useful for invasively monitoring an oxygen saturation level of blood in at least one tissue wall of an anatomical cavity, the probe comprising:
   a chassis having a proximal end and a distal end;
   an electrical connector extending from said proximal end of said chassis and terminating at a plug configured for connection to a pulse oximeter box;
   a reflectance optics assembly including an emitter assembly and a detector assembly and configured to generate and transmit electrical signals to said oximeter box, said signals being indicative of the oxygen saturation level of blood in the wall tissue; and
   a spring assembly attached to said chassis, wherein said emitter assembly and said detector assembly are attached to said spring assembly, and wherein upon deployment of said spring assembly, said emitter assembly and said detector assembly are urged into at least one tissue wall of the anatomical cavity, said spring assembly comprising:
      a first spring mechanism, said emitter assembly being operatively connected to said first spring mechanism;
      a second spring mechanism, said detector assembly being operatively connected to said second spring mechanism; and
      means for selectively controlling said first and said second spring mechanisms to thereby control the placement of said emitter assembly and said detector assembly along the length of said chassis.

23. A probe useful for invasively monitoring an oxygen saturation level of blood in at least one tissue wall of an anatomical cavity, the probe comprising:
   a chassis having a proximal end and a distal end;
   an electrical connector extending from said proximal end of said chassis and terminating at a plug configured for connection to a pulse oximeter box;
   a reflectance optics assembly including an emitter assembly and a detector assembly and configured to generate and transmit electrical signals to said oximeter box, said signals being indicative of the oxygen saturation level of blood in the wall tissue;
   a single spring mechanism attached to said chassis;
   a substrate suitably connected to said single spring mechanism, wherein said emitter assembly and said detector assembly are affixed to said substrate, and wherein upon deployment of said single spring mechanism, said emitter assembly and said detector assembly are urged into at least one tissue wall of the anatomical cavity; and
   means for selectively controlling said spring mechanism to thereby control the placement of said emitter assembly and said detector assembly along the length of said chassis.

* * * * *